(12) United States Patent
Bellman et al.

(10) Patent No.: US 10,272,284 B2
(45) Date of Patent: Apr. 30, 2019

(54) GAIT TRAINING APPARATUS FOR MEASURING SUPPORTED WEIGHT ON EACH SIDE OF A PATIENT IN REAL TIME AS THE PATIENT IS WALKING

(71) Applicant: Mobility Research, Inc., Tempe, AZ (US)

(72) Inventors: Ryan Bellman, Tempe, AZ (US); Amir Seif, Phoenix, AZ (US); Dave Dilli, Phoenix, AZ (US); Mohammed Ehsan, Phoenix, AZ (US)

(73) Assignee: Mobility Research, Inc., Tempe, AZ (US)

( * ) Notice: Subject to any disclaimer, the term of this patent is extended or adjusted under 35 U.S.C. 154(b) by 186 days.

(21) Appl. No.: 15/422,191

(22) Filed: Feb. 1, 2017

(65) Prior Publication Data
US 2018/0214336 A1    Aug. 2, 2018

(51) Int. Cl.
*A61B 5/11*     (2006.01)
*A61H 3/00*    (2006.01)
(Continued)

(52) U.S. Cl.
CPC .......... *A63B 22/0046* (2013.01); *A61B 5/112* (2013.01); *A61H 3/00* (2013.01); *A61H 3/008* (2013.01); *A63B 22/0235* (2013.01); *A63B 69/0064* (2013.01); *A63B 21/4009* (2015.10); *A63B 2022/0094* (2013.01); *A63B 2071/0652* (2013.01); *A63B 2220/50* (2013.01); *A63B 2220/52* (2013.01); *A63B 2225/50* (2013.01)

(58) Field of Classification Search
CPC ................ A61H 3/008; A63B 24/0062; A63B 22/0046; A63B 21/4009; A63B 2220/50; A63B 2022/0094
See application file for complete search history.

(56) References Cited

U.S. PATENT DOCUMENTS

| 5,569,129 A | 10/1996 | Seif-Naragni et al. |
| 6,302,828 B1 | 10/2001 | Martin et al. |
| (Continued) | | |

OTHER PUBLICATIONS

FreeDome Operator Manual published Aug. 4, 2015 by Mobility Research, Inc.

(Continued)

*Primary Examiner* — Sundhara M Ganesan
(74) *Attorney, Agent, or Firm* — Etherton Law Group, LLC

(57) ABSTRACT

A gait training apparatus for determining, in real time, how much weight is being supported on each side of the patient, even when the patient's shoulders are rotating as they do when walking. The apparatus employs two force sensors in an upper assembly that is connected to a supporting frame. The patient's harness is attached to a lower assembly which is rotatably suspended from the upper assembly. When a harnessed patient walks, the weight of each side of the patient is mechanically transferred from the rotating lower assembly to the force sensors on the non-rotating upper assembly. Each force sensor emits an electronic signal proportional to the load on the sensor, and enables the apparatus to measure in real time the weight supported on each side. A processing unit calculates the weight supported on each side of the patient and the total amount of the weight supported.

20 Claims, 7 Drawing Sheets

(51) Int. Cl.
*A63B 21/00* (2006.01)
*A63B 22/02* (2006.01)
*A63B 69/00* (2006.01)
*A63B 71/06* (2006.01)
*A63B 22/00* (2006.01)

(56) References Cited

U.S. PATENT DOCUMENTS

| | | | |
|---|---|---|---|
| 2005/0209065 A1* | 9/2005 | Schlosser | A61H 3/008 482/69 |
| 2014/0100491 A1* | 4/2014 | Hu | A61H 3/008 601/27 |
| 2014/0206503 A1* | 7/2014 | Stockmaster | A61H 3/008 482/4 |
| 2015/0306440 A1* | 10/2015 | Bucher | A63B 71/0054 482/4 |
| 2015/0320632 A1* | 11/2015 | Vallery | A61H 3/008 482/69 |
| 2016/0136477 A1* | 5/2016 | Bucher | A63B 22/02 482/4 |
| 2016/0158622 A1* | 6/2016 | Yamazaki | A63B 71/0054 482/7 |
| 2017/0165145 A1* | 6/2017 | Aryananda | A61H 3/008 |
| 2018/0071580 A1* | 3/2018 | Lee | A61H 3/00 |

OTHER PUBLICATIONS

LiteGait brochure, published by Mobility Research, Inc., downloaded from https://litegait.com/tech-support/documents/1076 on Feb. 1, 2017.

* cited by examiner

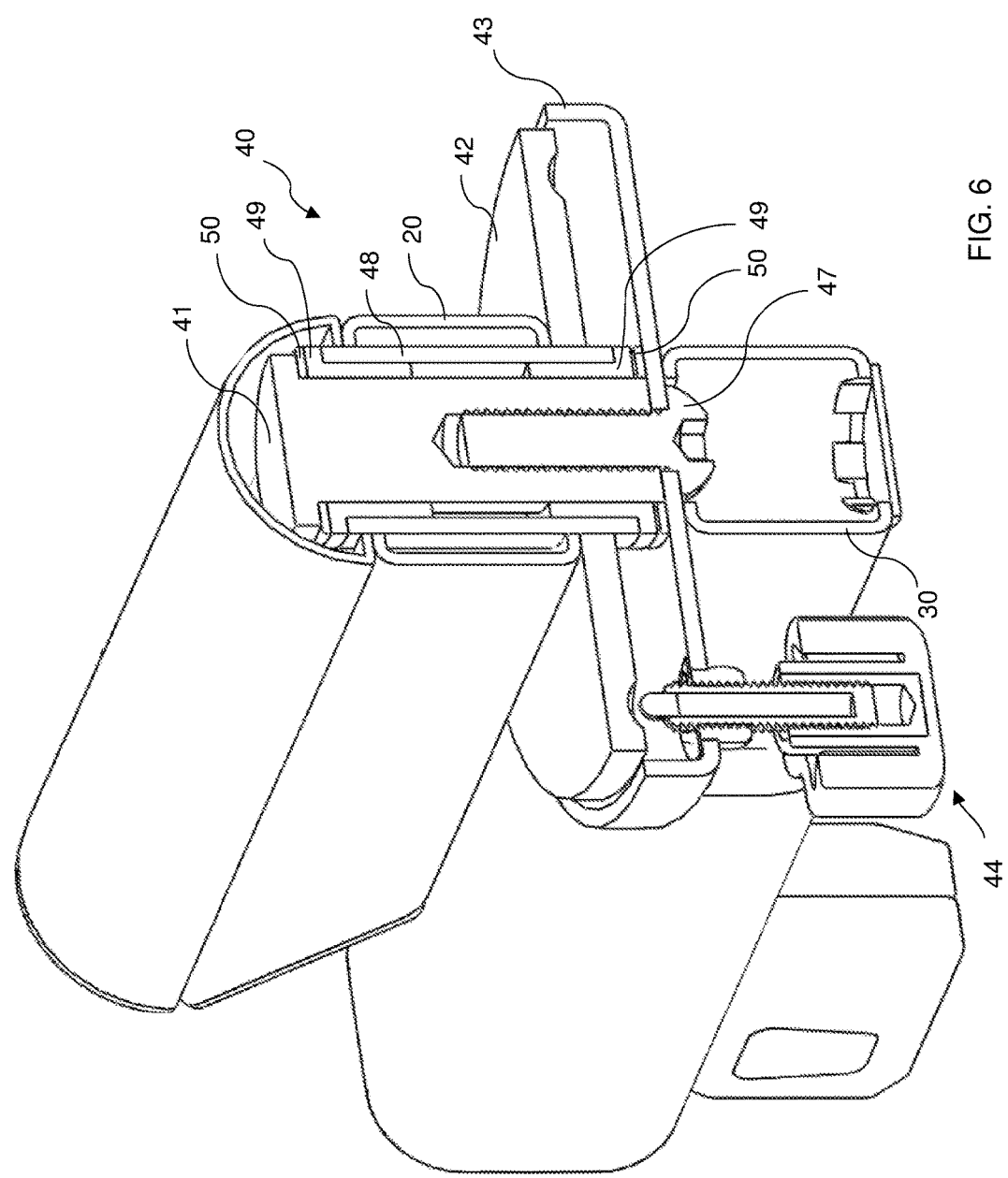

10,272,284 B2

GAIT TRAINING APPARATUS FOR MEASURING SUPPORTED WEIGHT ON EACH SIDE OF A PATIENT IN REAL TIME AS THE PATIENT IS WALKING

FIELD OF INVENTION

This invention relates generally to devices for gait training and more particularly to gait training devices that measure the supported weight on each side of the patient in real time as the patient walks.

BACKGROUND

Many patients have injuries to only one leg or to only one side of their body, and the injured side can support less weight than the other. This leads to uneven gait, weight-bearing asymmetry and postural imbalance. Partial weight-bearing gait training is a method of training a patient to walk in which the weight of the patient is partially supported by a harness device, and the amount of weight relief provided by the device for the patient is gradually reduced as the patient learns to support his own full weight while walking.

The shoulders of person with normal gait may rotate as much as 15 degrees while walking. It would be useful to know how much weight is being supported on each side of the patient while walking, as well as the total weight is being supported by the device. With this information the patient can use biofeedback and learn to support himself while walking and the therapist can better determine which aspects of the gait need to be treated.

Although walking forward is important, moving forward while taking backward steps and side-stepping are important for real-life success too. There are partial-weight bearing gait training devices that reduce the weight the patient is supporting, with an overhead movable platform that travels across a track installed in the ceiling or with a portable wheeled device. These devices utilize a single overhead cable to support the patient and do not provide different amounts of support for each side of the patient's body, nor can they measure how much weight is being supported on each side.

Another gait training device is disclosed in U.S. Pat. No. 5,596,129, which shares some of the co-inventors of the present invention. This device provides a partial weight-bearing gait training device that can be moved to different locations within a therapy facility or even between facilities. It also provides different amounts of support to each side of the patient. Unfortunately, however, it does not determine how much weight is being supported in real time on each side. This is one object of the present invention.

SUMMARY OF THE INVENTION

This gait training apparatus determines, in real time, how much weight is being supported on each side of the patient, even when the patient's shoulders are rotating as they do when walking. The gait apparatus employs two force sensors in an upper assembly that is connected to a supporting frame. The patient's harness is attached to a lower assembly which is rotatably suspended from the upper assembly. When a harnessed patient walks, the weight of each side of the patient is mechanically transferred from the rotating lower assembly to the force sensors on the non-rotating upper assembly. Each force sensor emits an electronic signal proportional to the load on the sensor, and enables the apparatus to measure in real time the weight supported on each side, so long as the lower assembly is within about 15 degrees of the upper assembly. A processing unit calculates how much weight is being supported on each side of the patient and the total amount of the weight supported.

BRIEF DESCRIPTION OF THE DRAWINGS

FIG. 6 is a partial cut-away perspective view of the hub.

DETAILED DESCRIPTION OF THE INVENTION

Figure 1:
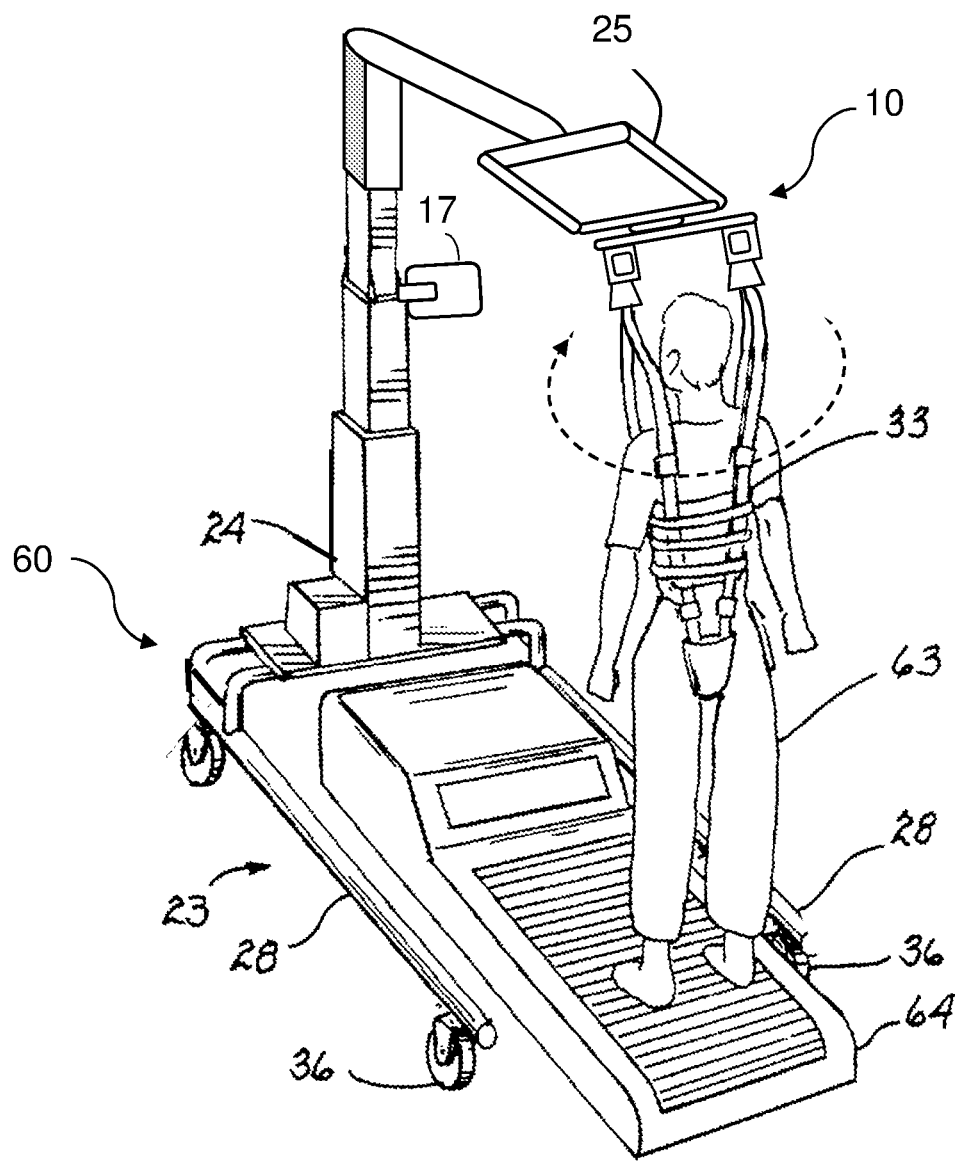
FIG. 1 is an illustration of a gait training apparatus of the present invention with a patient in a harness attached to the weight support assembly in a face-forward position.
Figure 2:
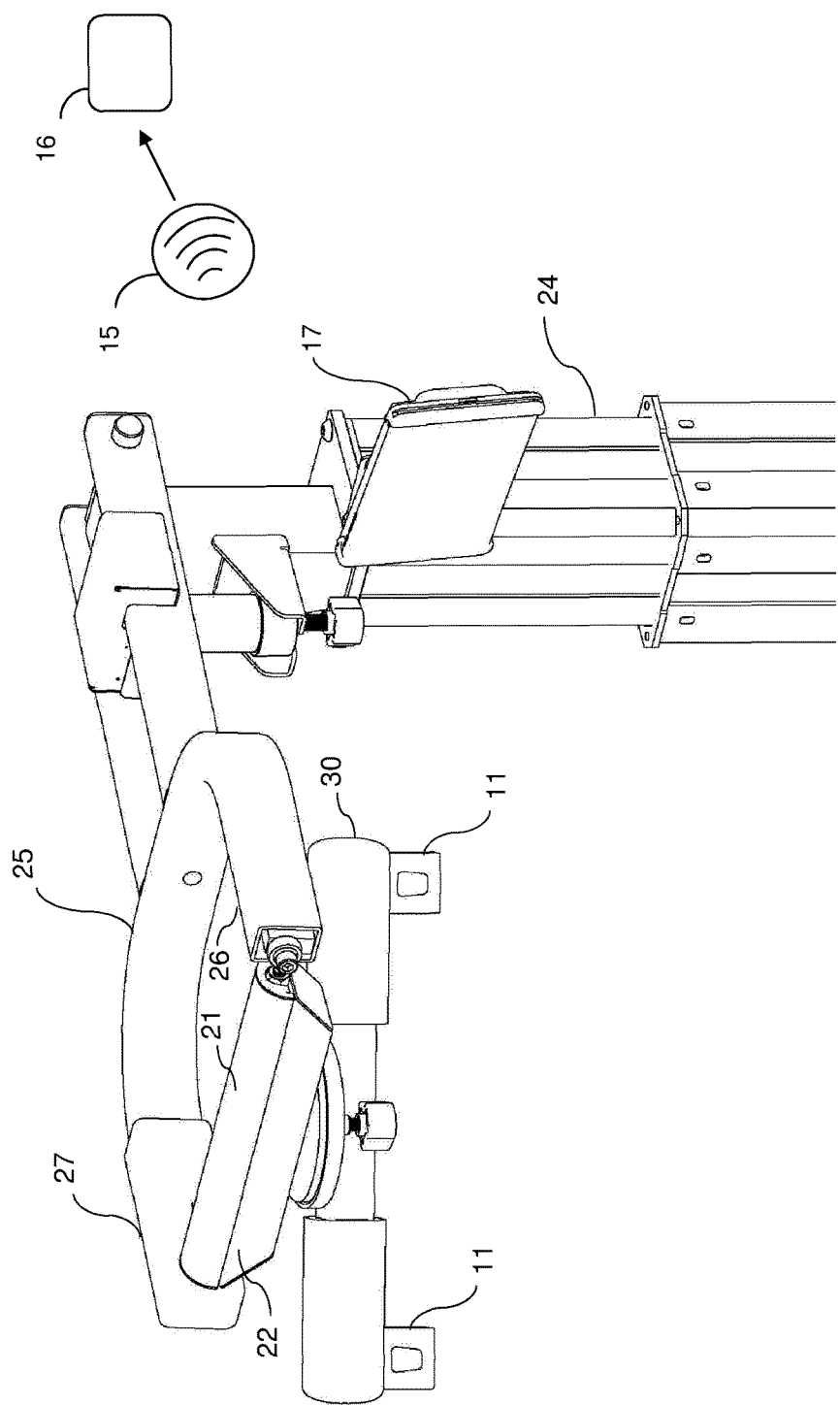
FIG. 2 is a perspective view of the weight support assembly attached to a yoke.
Figure 3:
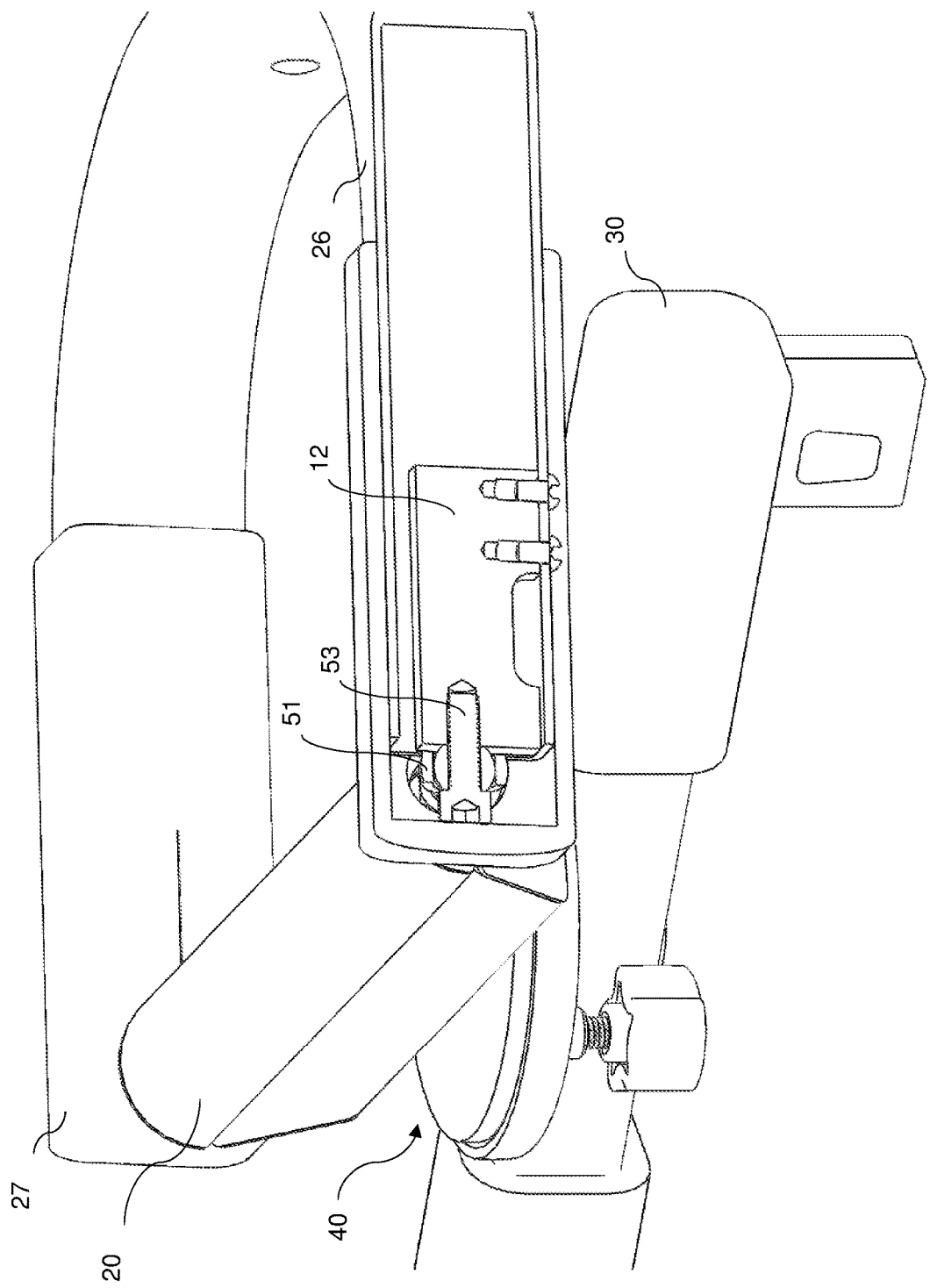
FIG. 3 is a partial cut-away perspective view of the first arm of the yoke showing a force sensor disposed in the yoke and connected to the upper assembly.
Figure 4A:
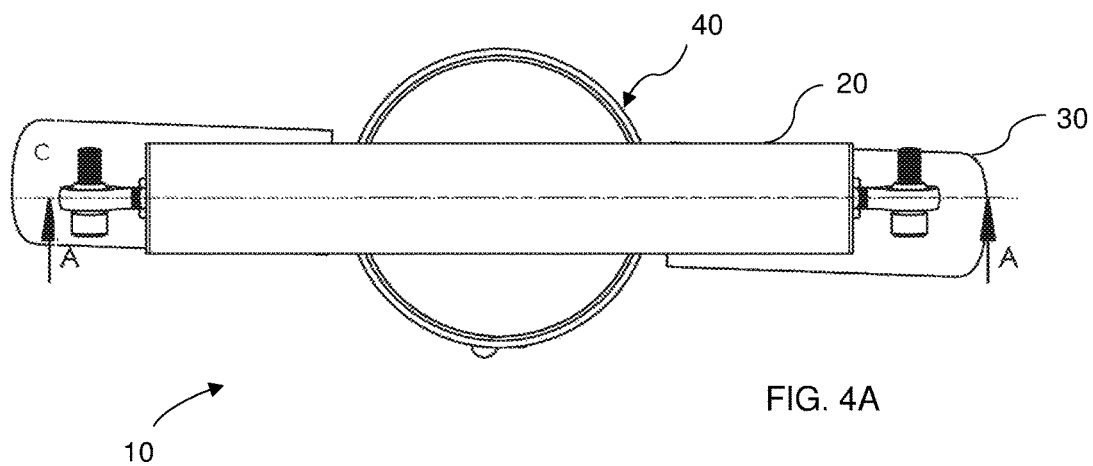
FIG. 4A is a top view of the weight support assembly in which the lower assembly is nearly parallel with the upper assembly.
Figure 4B:
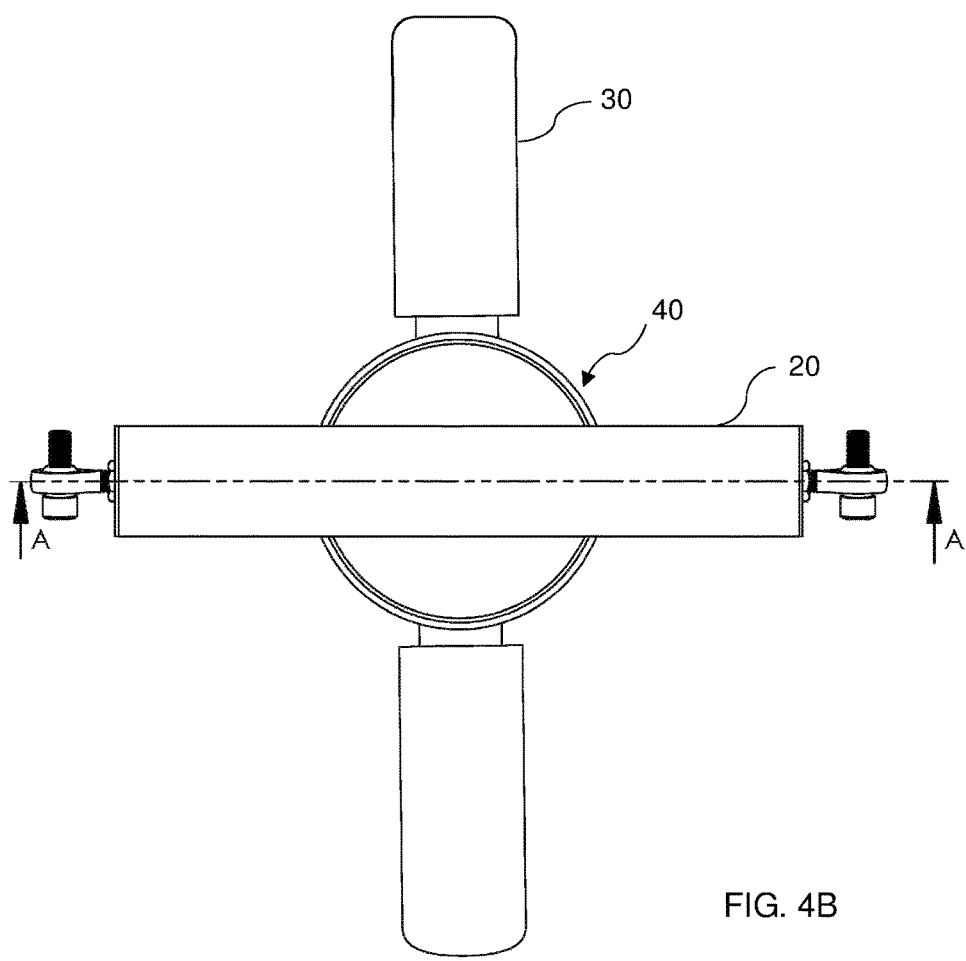
FIG. 4B is a top view of the weight support assembly in which the lower assembly is rotated 90 degrees from the upper assembly.
Figure 5:
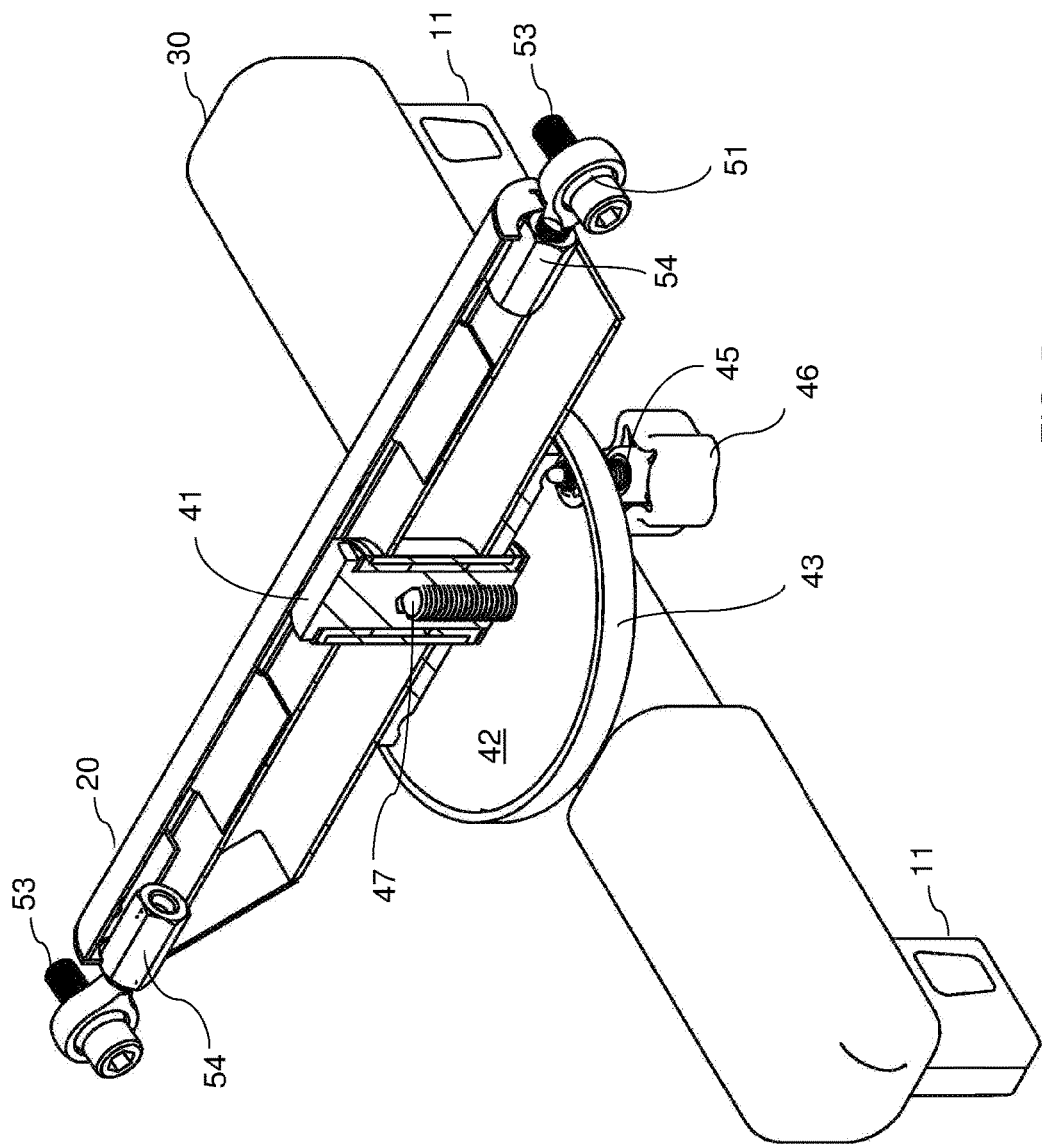
FIG. 5 is a partial cut-away perspective view of the weight support assembly of FIG. 3.

This gait training apparatus is illustrated in FIG. 1, in which a patient 63 is suspended in a harness 33 that is attached to a weight support assembly 10. The patient is shown in a face-forward position, with his shoulders roughly parallel to the upper assembly 20 and directly under fasteners 11 that attach the harness 33 to the weight support assembly 10.

The weight support assembly 10 comprises the upper assembly 20 that is rotatably connected at a hub 40 to a lower assembly 30. See FIGS. 2-5. A first force sensor 12 is connected to a first end 21 of the upper assembly 20 so that it supports the load on that end of the upper assembly. A second force sensor 13 is connected to the second end 22 of the upper assembly 20 and supports the load on that end of the upper assembly.

In a preferred embodiment each force sensor is disposed in or on the arm of a yoke 25. The yoke 25 supports the patient 63 from over each shoulder, maintaining posture and balance. This design allows measurement and control over the partial-weight bearing status of each side of the patient's body independently. Preferably the yoke is Y shaped, but can also be T, U or other shape so long as it has two points of attachment for the ends of the upper assembly.

Figure 7B:
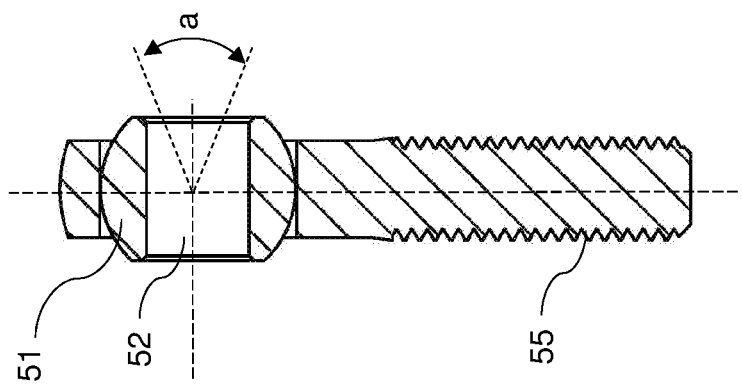
FIG. 7B is a cross-sectional view of a ball joint taken along line A-A of FIG. 7A.
Figure 7A:
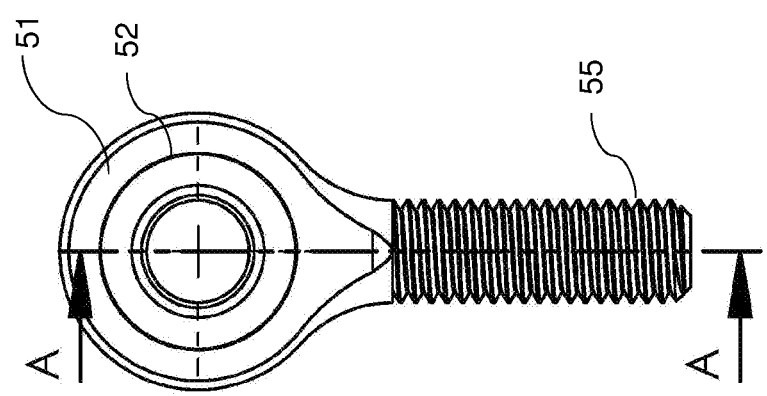
FIG. 7A is a top view of a ball joint.

The Y-shaped yoke 25 has two arms 26, 27. Each force sensor 12, 13 is attached to an arm 26, 27, respectively, preferably at a joint which permits some limited rotation to accommodate the patient drifting forward or backward slightly (if facing forward) relative to the force sensors and allow the vertical rotational axis to remain perpendicular to the ground when the yoke changes angles. Such rotational joints include shoulder screws, eye bolts and the like. Preferably the rotational joint is a ball joint 28, 29. FIGS. 7A and 7B show a ball joint 28 having a ball 51 with a through bore 52. Each ball joint is attached to a force sensor at its ball 51 by inserting a mounting screw 53 through the bore 52 into the force sensor. See FIG. 3. The other end of the ball joint, rod end 55, is attached to the upper assembly 20 by threading the rod end 55 into a matedly-threaded coupling nut 54. The presence of a rotational joint at each end of the upper assembly 20 creates an axis of rotation between the two spherical centers, which is coincident with the longitudinal axis of the rod ends of the ball joints. This rotational axis keeps the vertical rotational axis of the hub perpendicular to the ground, regardless of the angle of the yoke, which prevents a patient facing sideways from having his shoulders at different heights even if they were at the same height while facing forward. The suspended weight is free to rotate on the ball in this dimension until the mounting screw 53 interferes with the yoke 25. This movement is a relatively small amount, as designated by angle 'a' in FIG. 7B. If the device is rotated past this angular limit, 'a', the rod end 55 can rotate within the coupling nut 54, albeit with more friction and a very small amount of lateral translation compared to the movement at the ball 51. To prevent such additional rotation, the rod end 55 and coupling nut 54 may be locked together with a locknut (not shown).

Any form of force sensor may be utilized and they are available commercially. In a preferred embodiment a cantilever beam style load cell 14 is used, which works by deflecting a very small amount under load and measuring that deflection. One end of each load cell is fixed to the yoke and the other end is cantilevered out of the yoke very slightly so that it supports the load on that end of the upper assembly 20. See FIG. 3. Each force sensor emits an electronic signal proportional to the load on it. The sensor signals are received by a receiver 15 in a processing unit 16. The receiver is part of a data acquisition circuit, which amplifies and filters the signals, and then converts them to digital values. Preferably this is performed by a microprocessor. The data acquisition circuit is connected to a host system, such as a tablet, computer, smartphone, or other device having a user interface 17. Software installed on the host system may do additional computation and analysis. Communications may be made by wire or wirelessly. Preferably communications from the sensors to the processing unit are made by wire for highest performance. Communications between the processing unit and the host system are preferably wireless via USB, Bluetooth, or other wireless communication protocol. The device is preferably battery powered, but may be powered by mains. The processing unit (and by proxy the load cells themselves) are typically powered by the host system via a USB connection, but may also be powered by a separate battery, especially if wirelessly communicating to the host system.

The lower assembly 30 is rotatably attached to the upper assembly 20 at a hub 40, which is comprised of a number of cooperating, co-axial components. See FIG. 6. A circular hub tube 48 is fixedly attached inside the upper assembly 20 and has flanged plain bearings 49a and 49b installed at each end of it. These support both radial, thrust (axial), and moment loads between the hub tube 48 and the stem 41. The stem 41 extends coaxially from the upper assembly 20 through an upper detent plate 42, a lower detent plate 43, and the lower assembly 30. The stem 41 is fixedly attached to the lower assembly 30 with a pin 47 and rotates freely inside of the upper assembly 20. Preferably the stem 41 is threaded internally to mate with a threaded pin 47, which may be a bolt. To further reduce friction during rotation, a top thrust washer 50a is placed between the shoulder 41a of the stem and the flanged bearing 49 at the top of the hub 40. The shoulder 41a supports the axial (downward) load via the top thrust washer 50a and the top flanged plain bearing 49a. A lower thrust washer 50 rests on the lower detente plate 43, but it does not typically support load. Instead, it is there to function as a bearing and prevent damage, in case the device is misused by pushing upward while rotating. See FIG. 6.

The upper 42 and lower 43 detent plates rotate relative to each other unless locked together, and consequently the upper assembly 20 and lower assembly 30 also rotate relative to one another unless the detent plates are locked together. Preferably a detent system is used to lock the upper 42 and lower 43 detent plates together, although a clamp, through-pin, catch, dog, or other locking mechanism may suffice. A detent knob 44 is a threaded pin connected to a spring plunger 45 and a cap 46. The upper detent plate 42 has detents to receive the end of the pin which serves to retain the lower assembly 30 in a stationary position relative to the upper assembly 20. The detents are preferably concave recesses, but may be holes in the detent plate. If recesses are used the upper detent plate is typically thicker than the lower detent plate to accommodate the recesses. The lower detent plate 43 may be concave in order to hide the internal mechanism and to provide strength. When the detent knob 44 is partially disengaged by pulling or rotating the cap 45, the spring plunger pin pushes into these detents, causing the device to be biased to stay in the selected position. The rotating knob 44 can then be tightened, and the plunger compresses until the end of the threaded screw tightens into the detent, positively locking the lower assembly 30 from rotating relative to the upper assembly 20. The detent knob 44 can also be fully disengaged to eliminate the detent action for uninterrupted rotation.

Preferably the detents are placed at 90-degree intervals, but they can be placed at any position around the circumference of the detent plates. In this way the upper and lower assemblies can be locked in any relative rotation position allowing patient 63 to walk sideways, cross-step, backward, or simply walk with assistance when facing out of the apparatus.

Fasteners 11 depend from the lower assembly 30 for attaching the harness 33. In a preferred embodiment the fasteners 11 are the latch part of push-button automotive seat belt buckles which mate with a latch plate on the harness 33. Seat belt buckles are preferred because they are easy to disengage while proven to stay attached even under significant pull-apart force, such as with a very heavy patient falling while trying to walk. Other types of fasteners may suffice, such as D-rings, carabiners, snap hooks, spring hooks or the like. Once the harness 33 is fastened to the lower assembly the device prevents the patient from falling.

The harness 33 securely wraps around the patient's trunk and comfortably transfers load to the lower abdomen, over the hip, and through the groin. Optional thigh straps avoid loads to the groin area, but can interfere with limb movement. The groin straps promote full leg extension and prevents sitting. In the preferred embodiment the harness 33 has four adjustable straps that extend from the trunk portion over the head of the patient 63. Overhead adjustable straps allow correction of asymmetric upper body posture. Each of the straps can be individually adjusted to correct posture for proper walking. Adjusting the height of the harness 33 adjusts the amount of weight supported. Offloading a portion of a patient's weight during gait training allows the patient 63 to move freely, especially in a rotating manner, during the natural motion of walking and running and while applying reasonable constant force to prevent the patient 63 from falling if he's not yet able to support his weight.

In a preferred embodiment, the weight support assembly 10 is, via the yoke 25, attached to or integral with a center stanchion 24 of a center-stanchion frame 60, as shown in FIG. 1. The frame 60 has a U-shaped base 23 which enables unobstructed access to the patients' legs from the side and rear of the apparatus. The weight support assembly 10 can also be configured to be attached to an overhead rectangular frame, such as that shown in FIG. 1 of U.S. Pat. No. 7,468,023. That figure is incorporated herein by reference. Both types of frames permit a user to walk between side rails 58 on the floor or on a treadmill 64 that is positioned between the side rails 58. The weight support assembly 10 can be configured to be integral with a new gait training device or retrofitted to existing gait training devices. The apparatus may have wheels 36 for easy movement and does not require a track in the ceiling or permanent installation.

In either configuration, the upper assembly 20 is attached to the frame 60 and is relatively stationary with respect to the frame, except for the limited motion permitted by the joints. The lower assembly 30 rotates relative to the upper assembly 20. Supporting weight on the lower assembly 30 transfers the weight to the upper assembly 20 without wires, which permits free rotation without tangling wires, cables or harness straps.

With two force sensors, one on the left and one on the right end of the upper assembly 20, the apparatus can determine the amount of weight supported on each side of the patient 63 independently. The force sensors measure the weight supported at each end most accurately when the fasteners 11 are roughly underneath the force sensors. The more the patient 63 rotates, causing the lower assembly 30 to rotate more relative to the upper assembly 20, the less the left and right measurements correspond to the left and right weight support on the patient's body. In practice, these side weight measurements are most accurate when the orientation of the lower assembly is within about 15 degrees of the force sensors, which is sufficient for measuring supported side weight while walking. However, even if the force sensors do not accurately represent the load on each side of the patient when the force sensor is not above the point of patient support, the individual force sensor readings are accurate for what they are supporting, which between them is still the load applied by the patient. For greater accuracy, the angle of the lower assembly relative to the upper is measured and used to calculate the actual support on each side. The total weight supported can be calculated by summing the weight supported on each side. This total weight value is accurate at any position and can be determined while the patient 63 is dynamically rotating.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A gait training apparatus comprising:
   a) an upper assembly having a first end and a second end, the upper assembly comprising:
      i. a first force sensor connected to the first end which emits an electronic signal proportional to the load on the first end; and
      ii. a second force sensor connected to the second end which emits an electronic signal proportional to the load on the second end; and
   b) a lower assembly having a first end and a second end, the lower assembly rotatably connected to the upper assembly at a hub, the lower assembly comprising:
      i. a first fastener at the first end for connecting a harness; and
      ii. a second fastener at the second end for connecting the harness.

2. The apparatus of claim 1 further comprising a processing unit that receives the signals from the first and second force sensors to calculate the total amount of weight supported in the harness.

3. The apparatus of claim 1 wherein the processing unit calculates the amount of weight supported at the first end of the upper assembly and calculates the amount of weight supported at the second end of the upper assembly.

4. The apparatus of claim 1 wherein the hub comprises a stem, an upper detent plate, a lower detent plate, and a detent knob which cooperate to prevent the lower assembly from rotating relative to the upper assembly.

5. The apparatus of claim 4 further comprising:
   a) a top thrust washer, a first flanged plain bearing, and a second flanged plain bearing, and a pin, all coaxially arranged in a hub tube that is fixed to the upper assembly; and
   b) a pin mated to the stem to hold the lower assembly in co-axial alignment with the hub and upper assembly.

6. The apparatus of claim 1 further comprising a yoke wherein:
   a) the first force sensor and second force sensor are disposed on or in the yoke;
   b) the upper assembly is connected to the yoke at its first end and second end; and
   c) the yoke is connectable to a stanchion.

7. The apparatus of claim 6 further comprising a first rotational joint connecting the first force sensor to the upper assembly and a second rotational joint connecting the second force sensor to the upper assembly.

8. The apparatus of claim 6 wherein the yoke is connected to the stanchion such that the first force sensor and second force sensor are cantilevered from the stanchion.

9. The apparatus of claim 6 wherein the stanchion is connected to a U-shaped base such that the harness is suspended between the arms of the U.

10. A gait training apparatus comprising:
    a) a yoke having a first arm and a second arm, the yoke comprising:
       i. a first force sensor which emits an electronic signal proportional to the load on the first arm; and
       ii. a second force sensor which emits an electronic signal proportional to the load on the second arm;
    b) an upper assembly connected to the yoke between the first arm and second arm;
    c) a lower assembly having a first end and a second end, the lower assembly rotatably connected to the upper assembly at a hub, the lower assembly comprising:
       i. a first fastener for connecting a harness at the first end of the lower assembly; and
       ii. a second fastener for connecting a harness at the second end of the lower assembly.

11. The apparatus of claim 10 further comprising a harness configured to hold a patient's right shoulder under the first fastener and the patient's left shoulder under the second fastener.

12. The apparatus of claim 10 further comprising a processing unit that receives the signals from the first and second force sensors to calculate the total amount of weight supported in the harness.

13. The apparatus of claim 10 wherein the processing unit calculates the amount of weight supported at the first end of the upper assembly and calculates the amount of weight supported at the second end of the upper assembly.

14. The apparatus of claim 10 wherein the hub comprises a stem, an upper detent plate, a lower detent plate, and a detent knob which cooperate to prevent the lower assembly from rotating relative to the upper assembly.

15. A gait training apparatus for a body having a first side and a second side, the apparatus comprising:
   a) a stanchion;
   b) a yoke connected to the stanchion, the yoke having a first arm and a second arm;
   c) an upper assembly having a first end and a second end, the first end of the upper assembly connected to the first arm and the second end of the upper assembly connected to the second arm;
   d) a lower assembly having a first end and a second end, the lower assembly rotatably connected to the upper assembly at a hub;
   e) a hub comprising a stem, an upper detent plate, a lower detent plate, and a detent knob which can cooperate to prevent the lower assembly from rotating relative to the upper assembly;
   f) a first force sensor connected to the first arm which emits an electronic signal proportional to the load on the first end of the upper assembly; and
   g) a second force sensor connected to the second end which emits an electronic signal proportional to the load on the second end of the upper assembly.

16. The apparatus of claim 15 further comprising a processing unit that receives the signals from the first and second force sensors to calculate the weight supported by the first arm, the weight supported by the second arm, and the total amount of weight supported by the upper assembly.

17. The apparatus of claim 16 wherein the total amount of weight supported by the upper assembly is calculated while the lower assembly is rotating relative to the upper assembly.

18. The apparatus of claim 15 wherein the yoke is removable from the stanchion.

19. The apparatus of claim 15 further comprising a first rotational joint connecting the first arm of the yoke to the upper assembly and a second rotational joint connecting the second arm of the yoke to the upper assembly.

20. The apparatus of claim 19 wherein the first and second rotational joints are ball joints.

* * * * *